(12) United States Patent
Hagne et al.

(10) Patent No.: US 6,340,027 B1
(45) Date of Patent: Jan. 22, 2002

(54) EXTENSIBLE POLISHING MONO-FILAMENT DENTAL FLOSS

(75) Inventors: Leif Hagne, Liechtenstein; Lars Jönsson, Valdemarsvid, both of (SE)

(73) Assignee: Athena Nordic AB, Falun (SE)

(*) Notice: Subject to any disclaimer, the term of this patent is extended or adjusted under 35 U.S.C. 154(b) by 0 days.

(21) Appl. No.: 09/763,161

(22) PCT Filed: Aug. 16, 1999

(86) PCT No.: PCT/SE99/01376
§ 371 Date: Feb. 16, 2001
§ 102(e) Date: Feb. 16, 2001

(87) PCT Pub. No.: WO00/09034
PCT Pub. Date: Feb. 24, 2000

(30) Foreign Application Priority Data

Aug. 17, 1998 (CH) ............................................. 9802746

(51) Int. Cl.⁷ ............................................. A61C 15/00
(52) U.S. Cl. ..................... 132/321; 132/323; 132/329
(58) Field of Search ................................. 132/321, 323, 132/325–329, 200; 428/372, 375, 378, 394; 524/474, 476, 490, 505; 525/89, 95

(56) References Cited

U.S. PATENT DOCUMENTS 3,800,812 A    4/1974  Jaffe
5,806,539 A  * 9/1998  Blass et al. .................. 132/321
5,842,489 A  * 12/1998 Suhonen et al. ............. 132/321
6,003,525 A  * 12/1999 Katz ........................... 132/321
6,148,830 A  * 11/2000 Chen ........................... 132/321
6,161,555 A  * 12/2000 Chen ........................... 132/321
6,192,896 B1 * 2/2001  Tsao et al. ................... 132/321

FOREIGN PATENT DOCUMENTS

| EP | 0335466 | 10/1989 |
|----|---------|---------|
| EP | 0662388 | 7/1995  |
| WO | 9524167 | 9/1995  |

* cited by examiner

Primary Examiner—Pedro Philogene
(74) Attorney, Agent, or Firm—Dykema Gossett PLLC

(57) ABSTRACT

Monofilament dental floss/tape of polymer material including fluoride and polishing powder the dental floss/tape (1) being ribbon-shaped and having material properties that enable it to be stretched to increase its length by at least 100% and also to reduce its cross-sectional area by up to ten times, and also a method fot the use of monofilament polymer dental floss/tape (1) by preparing a suitable length of dental floss/tape (1) for cleaning the teeth , by extending it to a reduce cross section so that the area of the whole piece of floss/tape can thereafter be used to clean the teeth distally and/or mesially.

25 Claims, 1 Drawing Sheet

EXTENSIBLE POLISHING MONO-FILAMENT DENTAL FLOSS

TECHNICAL FIELD

The present invention relates generally to oral hygiene aids. More particularly the invention relates to a new type of flexible, polishing dental floss/tape that can actively remove plaque and discolouring between teeth, which is easy to use and is gentle to the gingival tissues.

BACKGROUND ART

Brushing the teeth is in itself not synonymous with cleaning the teeth and preventing caries/parodontitis. A toothbrush is only able to remove plaque on substantially facial and oral surfaces of the teeth. It has thus been shown that only approximately 60% of all tooth surfaces can be cleaned using a toothbrush and toothpaste. Since toothbrushes have poor interdental cleaning effect where parodontitis and caries often occur, various preventive aids exist for interdental cleaning, e.g. small "interdental bottlebrushes", dental sticks and dental floss/tape. All these preventive aids in principle lack any polishing effect such as that obtained by cleaning the teeth with toothpaste and toothbrush. A thoroughly efficient cleaning, including a certain polishing of the surface of the teeth on the 40% of the surface of the teeth out of reach of toothbrush and toothpaste is therefore difficult to perform. Cleaning the interdental spaces prior to brushing with a toothpaste containing fluorine is generally recommended, since the fluorine in the toothpaste is then better able to penetrate into the surface of the enamel interdentally also. Cleaning interdentally after brushing the teeth with fluorinated toothpaste would also deteriorate the effect of the fluorine since the time factor during which the fluoride ions remain on the teeth is extremely important for absorption of the fluorine into the enamel.

Dental floss/tape is preferably used in small/narrow interdental spaces with large gingival pockets where brushes, and often even dental sticks, are difficult to use due to lack of space.

Conventional dental floss/tape has a number of drawbacks both with regard to material and also to use. To enable its penetration of hard contact points between teeth, dental floss is made narrow and strong, and/or it is waxed so that it slides more easily through the contact point. Various sizes are available; narrow known as "dental floss" and wide known as "dental tape". Dental tape is able to clean a larger surface than dental floss. Dental floss has poor cleaning effect in large interdental spaces. Dental tape is always waxed, whereas dental floss may be waxed or unwaxed.

Investigations have shown that wax on dental floss or tape may adhere to the surface of the teeth. The wax may even prevent subsequent absorption in the dental surface of fluorine from the toothpaste. Dental floss without wax is therefore recommended to individuals with active caries. However, unwaxed floss does not slide as easily between the contact point and may therefore damage the gingival tissue if used too energetically. Several investigations have shown that fluoridated dental floss is the most efficient way of supplying fluorine at the contact points between the teeth, where caries most frequently occurs. It is considerably more efficient than only toothbrush and toothpaste and/or rinsing the mouth with NaF solution.

Since dental floss has no elasticity it may damage the gingival tissue and gingival pocket if used too hard and incorrectly, particular at hard contact points, which may be painful and cause bleeding. Multifilament floss, which often becomes saturated with bacteria when used, both on the surface and inside the floss around all the filaments, may even cause gingival inflammation by carrying bacteria into an injured gingival pocket. This is an important reason for many people tiring of using dental floss.

Conventional dental floss consists of myriad thin filaments twisted together. The floss often splits and remnants may fasten in the contact point.

When using conventional floss/tape without a dental floss holder, it may cut into the fingers in an unpleasant manner.

When cleaning interdental spaces with conventional floss, each tooth surface, distal and mesial, on the two teeth to be cleaned, must be cleaned individually which is a relatively complicated and time-consuming procedure. A bottlebrush is simpler to use since this cleans both surfaces simultaneously. The cleaning effect with dental floss, dental sticks and bottlebrushes is purely mechanical. No polishing effect or mild grinding effect, and thus the ability to remove not only plaque but also discoloration that smokers and tea drinkers suffer from interdentally, is thus available with the use of conventional dental floss, approximal brushes or dental sticks.

Through EP 0 662 388 it is already known to use polyethylene with high tensile strength for dental floss, Amongst other things, this patent specification shows a method of obtaining long products of thermoplastic. The specification also shows dental floss to be known that comprises a uniform filament of polyethylene having a molecular weight in the range of 300,000–6,000,000, a module of elasticity (Young's modulus) in the range of 0.5–10 GPa and a rupture point in the range of 0.1–1.2 GPa. Dental tape with these material properties is also known having a width in the range 0.01–0.25 inch (0.25–6.35 mm) and a thickness in the range 0.001–0.005 inch (0.025–0.13 mm).

This floss/tape is fully extended to just before its rupture point at the production stage, which means that it is uncomfortable to hold and is also inelastic in its longitudinal direction, as well as its cross-sectional area being determined immediately after the production stage. This floss/tape also lacks polishing agent and is therefore unable to remove discoloration between the teeth caused by tea, chewing tobacco, snuff or tobacco smoke.

EP 0 335 466 refers to a dental floss having many filaments. Bacteria can penetrate into the actual floss in a multifilament floss. This makes it difficult to rinse away plaque and bacteria from the surface or interior of the floss in a simple manner under the tap while standing over the basin to clean the teeth. This can be noticed because floss made of many thin filaments smells unpleasant after being used for a while in an unclean mouth, even if attempts are made to rinse it under the tap. A new length of floss must therefore usually be taken. What is unique about this floss is combining filaments of expanded Teflon with a microcrystalline wax, the main purpose of which is to reduce the friction coefficient. This floss is also thin and thus uncomfortable to hold, as well as being inelastic, which means that its cross-sectional area is determined immediately after the production stage. Nothing is stated in the claims of this patent concerning the addition of a polishing abrasive agent. Instead, the low friction coefficient of the floss due to the Teflon//wax content is emphasised. It must be supposed that the polishing effect from dental floss treated with Teflon and having low friction coefficient is negligible.

OBJECT OF THE INVENTION

The object of our invention is to provide a completely new dental floss/tape having material properties allowing it to be dimensioned before use to fit different types of interdental spaces by means of a stretching procedure. Another object is that the material properties are such that the dental floss/tape is hardened by means of the stretching procedure. Another object is to provide a dental floss/tape that has different friction coefficients in stretched and unstretched state. In stretched state the floss/tape is very thin and has a low friction coefficient allowing it to easily penetrate contact points between the teeth. The considerably less stretched part of the floss/tape gives a high friction coefficient by having been mixed with a polishing abrasive such as silica or aluminium oxide. Since in unstretched state the floss/tape is given a high friction coefficient it can efficiently remove not only plaque but also discoloration between the teeth. Yet another object is to provide dental floss/tape having low friction coefficient but which is not provided with a surface coating of wax, for instance.

SUMMARY OF THE INVENTION

The object of the invention is fulfilled by means of the present invention as defined in the characterizing parts of the claims, and all the drawbacks mentioned above are eliminated.

Amongst other things, the idea of our dental floss/tape is to sell floss/tape in unstretched state, i.e. to leave adjustment of the floss/tape by means of stretching, to the consumer. The floss/tape shall be easy and pleasant to hold, without cutting into the fingers causing the tips of the fingers to become blue from congestion of blood. Stretching can thus regulate the thickness of the floss/tape in relation to the contact point to be penetrated and the interdental space to be cleaned. It is also important to point out that our floss/tape is elastic and that since, through the addition of polishing powder, it is not stretched along its whole length during use, the surface is slightly abrasive so that plaque (dental deposits) can easily adhere to it and it also has a mildly polishing effect. The surface of our floss/tape can easily be rinsed with warm or cold water during use to avoid carrying odorous. pathogenic bacteria from one interdental space where the gingival pockets are infected with gingivitis or parodontitis, to a healthy interdental space. Our floss/tape can even be rinsed and used for several days if so desired.

The material in the floss/tape is a polymer material, preferably from the polyether block amide (PEBA) group of materials. e.g. a material marketed under the trademark PEBAX®, or material with similar properties.

Our floss/tape shall preferably have an abrasive mixed into it in order to remove discoloration between the teeth. The quantity of abrasive and its abrasivity/polishing effect shall be determined by means of RDA tests or the equivalent. RDA testing is an extremely accurate method of measuring the abrasive effect of a toothpaste, for instance. Further information concerning RDA (Radioactive Dentine Abrasivity) can be found in the literature. It will be understood that, for the consumer, it may be an advantage to see how high the abrasive effect of the floss/tape is in comparison with toothpaste, for instance. Normal, low-abrasive toothpaste is between 30 and 40. One version of our floss/tape intended for people with troublesome dental deposits and/or for use on patients by dental staff shall have a RDA effect of at least 50. Floss/tape variants with built-in abrasive in accordance with the invention, are thus RDA-determined with regard to abrasivity.

The most important variant of floss/tape within the scope of our invention is floss/tape with a combination of fluorine and silica (an abrasive) built into the floss/tape similarly to toothpastes containing these substances.

Since the material in the floss/tape is tough, the stretched part slides easily through the contact point between the teeth, does not damage the gingival tissue, does not shred, can be adjusted as to thickness and can very efficiently remove plaque in its unstretched part, with a polishing effect similar to that of toothpaste plus toothbrush, a new type of floss/tape is obtained with a polishing effect that is more efficient and simpler to use than conventional floss/tape. The material is non-toxic. without problems from the environmental aspect, and inexpensive to manufacture.

BRIEF DESCRIPTION OF THE DRAWINGS

The invention will now be described in more detail with reference to the accompanying drawings.

DESCRIPTION OF THE INVENTION

Figure 1:
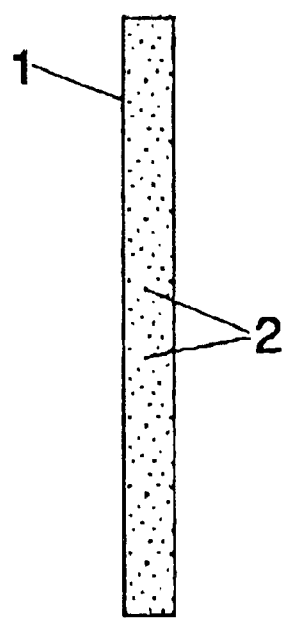
FIG. 1 shows a piece of dental tape in accordance with the present invention.

FIG. 1 shows a piece of dental tape 1 in unstretched state, ready for delivery, with small patches or a pattern of abrasive 2, such as silicon dioxide, in its surface. In this state the tape is not ready/prepared for use. A suitable width for the tape in this state is approximately 2.0 mm.

Figure 2:
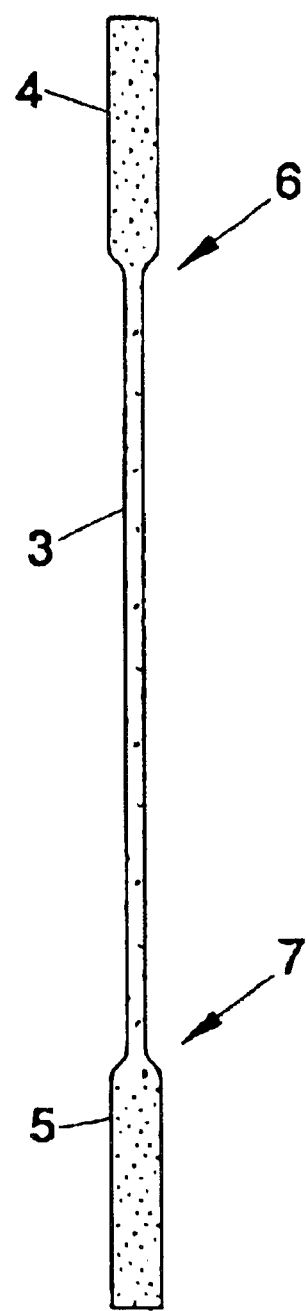
FIG. 2 shows the same piece of dental tape as in FIG. 1, its mid-section having been stretched and obtained a permanent plastic deformation

FIG. 2 shows the same tape as in FIG. 1 that has been made ready for use by its mid-section 3 being stretched out and thus plastically deformed. It is now sufficiently thin to easily penetrate the contact point between two teeth. The tape has thereby obtained two end portions 4, 5, functioning as gripping areas, said end portions continuing into the mid-section 3 via two deformation zones 6, 7. Since the tape is stretched, the quantity of abrasive in the surface of the tape is less, which means that the friction is also less in this part. The material per se has self-lubricating properties which are improved when it is extended in this way. The thicker end portions 4, 5 of the tape are also used to clean and polish the interdental space.

The favourable properties distinguishing dental tape in accordance with the invention are due partly to the shape, partly to the additives such as fluorine and abrasive combined into the material, and partly to the use of the tape.

By manufacturing the dental tape from a polymer material, in strips of up to 6.0 mm in width, preferably 1.0–3.0 mm, a dental tape is obtained having a shape forming the basis of the properties that are decisive to the invention. The width of the dental tape in unstretched state is thus 1.0–3.0 mm and its thickness in unstretched state is 0.1–0.4 mm.

As mentioned above, the material constitutes polymers, preferably from the polyether block amide (PEBA) group of materials, e.g. those marketed under the trademark PEBAX®, or material with similar properties. PEBAX® comprises material having the general formula:

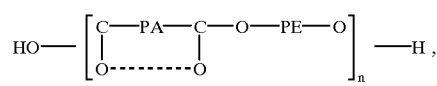

where PA denotes a polyamide segment and PE denotes a polyether segment. PEBAX® also covers materials that are soft and flexible, but at the same time tough and strong. The material is also tensile and, in its extended state the material becomes even stronger. Stretching should be performed relatively slowly in order to avoid rupture. Characteristic properties of these materials are that they consist of a monofilament polymer material, i.e. the material is homogenous. Furthermore, dental floss/tape manufactured of such material, can be extended to increase its length by 100–800% and simultaneously reduce its cross-sectional area by up to ten times. The extension before rupture occurs is 100–1000%. It is important that, after stretching, the tape obtains a certain amount of permanent plastic deformation. As a result of this plastic deformation the material will also harden. The modulus of elasticity of the material is 10–100 Mpa, preferably 25 Mpa, its modulus of extension is 10–50 Mpa, preferably 30 Mpa, and if PEBAX® is used, its rupture limit will appear at an extension of 670%. These moduli can be varied in the manufacturing process so that the dental tape obtains suitable properties for different areas of use, i.e. "pure dental floss" and "tape for removing discoloration", etc.

When the material is incinerated the main components produced are carbon dioxide and water which is advantageous from the environmental aspect since dental floss made from the material is usually a disposable product.

Dental floss/tape manufactured of such material is considerably less expensive to produce than conventional dental floss/tape and can therefore be sold to the consumer more cheaply.

Since dental floss/tape made of such material is not composed of a multitude of thin filaments intertwined, it cannot shred or fray and become lodged in the contact point in the same way as conventional floss/tape. It will also be understood that bacteria cannot Penetrate into a monofilament tape in the same way as in a conventional multifilament dental floss, and that our tape is therefore easier to keep clean from plaque during use by rinsing it with hot or cold water.

Dental tape in accordance with the invention is used in the following manner.

A length of the stated polymer material approximately 10 cm is stretched in the middle so that the mid-section is plastically deformed, extended and becomes thinner. The tape then has a thin mid-section having slight cross section, and two outer portions having greater cross section. The thin mid-section is used to penetrate the contact point, and the outer thirds are used for cleaning the space between two teeth. An area of a piece of dental tape of suitable length is thus prepared for cleaning the teeth by being extended to a reduced cross section for the area or the whole piece of tape to be used for cleaning the teeth distally and/or mesially. Prior to stretching the ends of the piece of tape are preferably wound around at least one finger on each hand, and the stretching is then performed.

The thin mid-section, which is also strengthened by the stretching process, is passed with a gentle sawing movement between the contact point between the teeth whose interproximal space is to be cleaned. The tape is then withdrawn slightly from the interdental space in facial or oral direction and one of the two outer thicker parts of the tape is used to efficiently clean and polish the interdental space. These thick outer thirds of the tape will act in approximately the same way as a bottlebrush, i.e. the distal and mesial surfaces on the two teeth to be cleaned interproximally will be simultaneously cleaned when the tape is withdrawn from the interdental space. This greatly simplifies the manual manipulation of the tape and also saves time. Furthermore, the 40% of the tooth surfaces that are not reached by toothbrush and toothpaste can be polished, thanks to the abrasive powder contained in the tape.

If the outer, cleaning parts of the tape are too thick, they can be adjusted by being pulled out somewhat so that they become thinner and fit better into small interproximal spaces. The need for various types of aids, such as dental sticks and interproximal bottlebrushes, depending on the size of the interdental spaces is thus reduced since the thickness of the tape can be adjusted by stretching. The only two aids necessary for effective cleaning and polishing, as well as the supply of fluorine to the contact points also, are therefore our tape and a toothbrush with fluoridated toothpaste.

The polymer dental tape slides easily through the contact point without having to be waxed since the surface of the material has self-lubricating properties. It is thus unnecessary to wax the surface on this tape for it to be able to slide through the contact point better. The problem of hindering absorption of the fluorine from fluoridated toothpaste due to wax remnants on the tooth surface is thus eliminated. Since this dental tape can be made thinner than conventional floss/tape its penetration of the contact point is also facilitated.

The polymer dental tape also has another extremely important property that makes it superior to conventional floss/tape: plaque adheres much better on the surface of the polymer tape than on conventional floss/tape. This is probably due to electrical phenomena and to its surface structure.

Bacteria and glucoproteins on the surface of the teeth are negatively charged. Due to the frictional electricity that arises when the polymer tape is drawn through the interdental space. electrons are removed from the material and the tape becomes positively charged. Negatively charged bacteria and glucoproteins are then attracted and adhere to the now positively charged tape. The surface of the tape is provided with irregularities and minute particles of abrasive protruding from the surface for increased cleaning and polishing effect. The surface thus produces a polishing effect similar to that of toothbrush and toothpaste. For people with troublesome deposits the abrasivity in the tape can be increased by the addition of coarser abrasive powder. The tape's content of polishing powder is an important factor for its cleaning capacity.

Conventional floss/tape has a relatively smooth surface without polishing agent. The cleaning effect of such a floss/tape is thus poorer than of toothbrush plus toothpaste and the interdental spaces are therefore often discoloured despite assiduous use, particularly in the case of smokers.

Even with relatively hard use of this dental tape the risk of injuring the gingival tissue is substantially eliminated. In the first place the rupture limit is lower than for conventional floss/tape, which means that the tape simply breaks if it is used too vigorously. Secondly, the tape is extensible so that when it encounters the gingival tissue during too vigorous use, it will stretch so that penetration into the gingival tissue is eliminated, or the tape will break when it encounters the gingival tissue. A thin, rigid (in this respect similar to a piano wire), conventional floss/tape penetrates into the gingival tissue and damages it if used too vigorously.

The thicker, outer thirds of the tape are easier to grip with the fingers and hands then a conventional, thin piece of floss/tape. Furthermore, the unstretched part of our tape does not slip so easily between the fingers, or "against itself", since the silica increases the friction in the unstretched part of the tape. The polymer material has the additional advantage that it does not cut into the fingers in the same way as conventional floss.

A decisive advantage of manufacturing dental tape using extrusion technology similar to that used in producing spaghetti is that elastomeric material such as PEBAX® can be used, into which other desirable substances, e.g. silica and fluorine, can easily be mixed during the production phase. PEBAX® can also be impregnated with various substances after the production phase, since the tape has a water absorption of 1% for 24 hours.

We have shown that fluorine which has been combined with the tape during the production phase is released at a uniform rate and over a long period of time, contrary to conventionally fluorine-impregnated floss where the fluorine effect diminishes extremely rapidly. It is therefore unnecessary to think about using different parts of the tape in order to obtain adequate fluorine emission to the contact point and interproximal space that is cleaned last.

Furthermore, our dental tape is the only floss/tape that has polishing agent (currently silica), combined in the material, and thus the only one with polishing ability. The abrasivity/polishing effect of the tape will be precisely determined and stated on the package so that comparison can be made with the toothpaste the consumer uses.

Using extruder technology the floss can be given tape shape, i.e. large width and small thickness. This enables the ratio surface/cross-sectional area to be large in comparison with circular floss, and a larger part of the added fluorine and abrasive will therefore come into contact with the tooth than if the floss had been circular in cross section.

The dental floss/tape is manufactured by extruding the raw material, in the form of a dough-like lump, through a nozzle of suitable shape and then cooling it in water. The cooling produces a floss/tape with less rubber-like properties. The raw material must be kept dry prior to extruding since it is able to absorb moisture from the air. Sacks of the raw material must be sealed and material extruded must be dried in a special material drier before use. Since the material has high friction it has a tendency to stick together during production unless it is taken care of immediately. Since the material is transparent, a high degree of cleanliness must prevail around the work place when the finished product is being handled. The degree of absorption of the finished dental floss/tape is 1% water for 24 hours, which means that additives can be deposited on the surface of the floss/tape after extruding instead of being combined into the floss/tape before extrusion.

Another embodiment of the dental floss/tape is obtained by combining or high-pressure spraying the floss/tape with cotton or synthetic fibres having a fibre length of 1–3 mm after extrusion, while the floss/tape is still hot. The result of the procedure is a "fur-like" tape suitable for patients with large approximal spaces. The fibres may protrude approximately 0.5–1.5 mm from the surface of the floss/tape.

Embodiments of the floss/tape provided with flavour additives, giving a flavour of peppermint or cherry, for instance, are also possible. Other embodiments include treating the surface layer with fluoride which is arranged to be deposited on the teeth during use. Alternatively the floss/tape may be combined with fluorine, which greatly increases the period during which fluorine is released to the teeth. Yet other embodiments entail treating the surface layer of the floss/tape with one or more plaque-inhibiting substances such as chlorhexidine or listerine which, upon use of the floss/tape, is arranged to be deposited on the teeth. Embodiments also exist where the surface of the floss/tape is impregnated with sodium bicarbonate, which acts as bleaching agent. Embodiments also exist where the floss/tape has been treated with xylitol in order to eliminate streptococci on the tooth surface at an early stage and also to act as a flavour additive. Also falling within the scope of the invention are embodiments where the surface layer of the floss/tape is impregnated with an abrasive substance with an RDA effect of at least 50 to remove discoloration between the teeth. Embodiments where the floss/tape is coloured to suit a certain flavouring of the floss/tape, e.g. orange coloured tape with orange flavour, are also possible.

The properties mentioned above are intended, either individually or in combination, to constitute advantageous variants of the present dental floss/tape.

What is claimed is:

1. Monofilament dental floss/tape of polymer material, characterized in that the dental floss/tape (1) is arranged to be stretched to a permanent deformation prior to its use, in order to increase its length and also reduce its cross-sectional area.

2. Dental floss/tape as claimed in claim 1, characterized in that the permanent deformation of the dental floss/tape (1) prior to use is 100–800%.

3. Dental floss/tape as claimed in claim 1 characterized in that the cross-sectional area of the dental floss/tape (1) is reduced by up to ten times upon stretching.

4. Dental floss/tape as claimed in claim 1, characterized in that the dental floss/tape (1) is made of a polymer material which is work-hardened upon being stretched.

5. Dental floss/tape as claimed in claim 1, characterized in that the dental floss/tape (1) is ribbon-shaped.

6. Dental floss/tape as claimed in claim 1, characterized in that the modulus of elasticity lies within the interval 10–100 Mpa.

7. Dental floss/tape as claimed in claim 6, characterized in that the modulus of extension lies within the interval 10–50 Mpa.

8. Dental floss/tape as claimed in claim 7, characterized in that the extension before rupture is 100–1000%.

9. Dental floss/tape as claimed in claim 1, characterized in that the material in the dental floss/tape (1) belongs to the polyether block amide (PEBA) group of materials.

10. Dental floss/tape as claimed in claim 9, characterized in that the material in the dental floss/tape (1) follows the general formula,

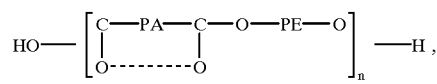

where PA denotes a polyamide segment and PE denotes a polyether segment.

11. Dental floss/tape as claimed in claim 9, characterized in that the width of the dental floss/tape (1) in unstretched state is 1–3 mm and that the thickness of the dental floss/tape (1) in unstretched state is 0.1–0.4 mm.

12. Dental floss/tape as claimed in claim 1, characterized in that its surface structure is provided with irregularities and/or a pattern for heightened cleaning effect.

13. Dental floss/tape as claimed in claim 1, characterized in that the floss/tape (1) is provided with an addition of silicon dioxide that has a polishing action on the surface of a tooth.

14. Dental floss/tape as claimed in claim 1, characterized in that the floss/tape (1) is provided with a flavour additive to give it a flavour of peppermint or cherry, for instance.

15. Dental floss/tape as claimed in claim 1, characterized in that the floss/tape (1) is provided with a colouring agent.

16. Dental floss/tape as claimed in claim 1, characterized in that the floss/tape (1) has fluoride included in the floss/tape material which, when the floss/tape (1) is used, is designed to be deposited on the teeth.

17. Dental floss/tape as claimed in claim 1, characterized in that the outer layer of the floss/tape (1) is treated with one or more plaque-inhibiting substances, e.g. chlorhexidine or listerine which, upon use of the floss/tape, is arranged to be deposited on the teeth.

18. Dental floss/tape as claimed in claim 17, characterized in that the outer layer of the floss/tape (1) is impregnated with an abrasive substance having an RDA effect or at least 30 or includes a grinding powder to the equivalent effect.

19. Dental floss/tape as claimed in claim 1, characterized in that the outer layer of the dental floss/tape (1) is provided with cotton or synthetic fibres having a fibre length of 1–3 mm.

20. Dental floss/tape as claimed in claim 1, characterized in that the floss/tape (1) is treated with xylitol.

21. A method for the use of monofilament polymer dental floss/tape, characterized in that an area of a piece of dental floss/tape (1) of suitable length is prepared for cleaning the teeth by being stretched out with permanent deformation, to a reduced cross section so that the area, or the whole piece of floss/tape can then be used to clean the teeth distally and/or mesially.

22. A method of producing monofilament polymer dental floss/tape, characterized in that a raw polymer material is extruded through a nozzle of suitable shape and thereafter cooled in water.

23. A method as claimed in claim 22, characterized in that additives are deposited on the surface of the floss/tape (1) after extrusion.

24. A method as claimed in claim 22, characterized by combining or high-pressure spraying the floss/tape (1) with cotton or synthetic fibres having a fibre length of 1.0–3.0 mm.

25. A method as claimed in claim 22, characterized in that the additives are combined in the raw material for the floss/tape (1) prior to extrusion.

* * * * *